(12) United States Patent
Consolaro et al.

(10) Patent No.: US 9,457,506 B2
(45) Date of Patent: Oct. 4, 2016

(54) PROCESS FOR PRODUCING AND ASSEMBLING A MEDICAL OPERATIONS SYRINGE

(75) Inventors: Roberto Consolaro, Arzignano (IT); Rajeev Kabbur, Montebello Vicentino (IT)

(73) Assignee: BREVETTI ANGELA S.R.L., Arzignano (VI) (IT)

( * ) Notice: Subject to any disclaimer, the term of this patent is extended or adjusted under 35 U.S.C. 154(b) by 1068 days.

(21) Appl. No.: 13/381,877

(22) PCT Filed: Jul. 2, 2010

(86) PCT No.: PCT/IT2010/000295
§ 371 (c)(1),
(2), (4) Date: Mar. 19, 2012

(87) PCT Pub. No.: WO2011/001456
PCT Pub. Date: Jan. 6, 2011

(65) Prior Publication Data
US 2012/0167528 A1    Jul. 5, 2012

(30) Foreign Application Priority Data

Jul. 3, 2009  (IT) .............................. VI2009A0160

(51) Int. Cl.
*B65B 3/02*         (2006.01)
*B29C 49/20*        (2006.01)
(Continued)

(52) U.S. Cl.
CPC ............ *B29C 49/20* (2013.01); *A61B 5/1411* (2013.01); *A61B 5/153* (2013.01);
(Continued)

(58) Field of Classification Search
CPC .......... B65B 3/003; B65B 3/022; A61J 1/06; A61J 1/067; A61M 5/24; B29C 49/20; B29C 49/76; A61B 5/150274; A61B 5/150297
USPC ................ 53/452, 453, 559, 561, 471, 281; 264/239, 294, 296, 297.1, 297.2, 299; 29/428
See application file for complete search history.

(56) References Cited

U.S. PATENT DOCUMENTS 4,539,172 A *  9/1985  Winchell et al. ............. 264/515
4,904,437 A *  2/1990  Muhlbauer .................... 264/295
(Continued)

FOREIGN PATENT DOCUMENTS

| DE | 4420 594 A1 | 12/1995 |
|----|----|----|
| WO | WO 2007/007178 A1 | 1/2007 |
| WO | WO 2007007178 A1 * | 1/2007 |

OTHER PUBLICATIONS

PCT Search Report Dated Jun. 22, 2011.
(Continued)

*Primary Examiner* — Stephen F Gerrity
*Assistant Examiner* — Joshua Kotis
(74) *Attorney, Agent, or Firm* — Hedman & Costigan, P.C.; James V. Costigan; Kathleen A. Costigan (57) ABSTRACT

A process for producing and assembling a medical operations syringe (20) comprising in the order the operations of extruding plastic material in order to obtain an intermediate tubular element (1) made of plastic material at least partially at molten state, performing on the intermediate tubular element (1) a blow molding in order to obtain at least a hollow body (2), inserting firmly and at least partially a thrust piston (3) into the hollow body (2) immediately after the blow molding operation.

16 Claims, 3 Drawing Sheets

(51) Int. Cl.

| | |
|---|---|
| *B29C 49/08* | (2006.01) |
| *A61B 5/15* | (2006.01) |
| *A61B 5/153* | (2006.01) |
| *A61M 5/00* | (2006.01) |
| *A61M 5/28* | (2006.01) |
| *B29C 49/76* | (2006.01) |
| *B65B 3/00* | (2006.01) |
| *B65B 7/16* | (2006.01) |
| *A61M 5/31* | (2006.01) |
| *B29C 39/04* | (2006.01) |
| *B29C 49/46* | (2006.01) |
| *B29L 31/00* | (2006.01) |

(52) U.S. Cl.
CPC .. *A61B 5/150236* (2013.01); *A61B 5/150297* (2013.01); *A61B 5/150351* (2013.01); *A61B 5/150389* (2013.01); *A61B 5/150519* (2013.01); *A61B 5/150618* (2013.01); *A61M 5/002* (2013.01); *A61M 5/28* (2013.01); *B29C 49/76* (2013.01); *B65B 3/003* (2013.01); *B65B 7/161* (2013.01); *A61B 5/15003* (2013.01); *A61B 5/150244* (2013.01); *A61B 5/150717* (2013.01); *A61M 2005/312* (2013.01); *A61M 2005/3121* (2013.01); *B29C 39/04* (2013.01); *B29C 2049/4697* (2013.01); *B29C 2791/001* (2013.01); *B29L 2031/7544* (2013.01); *Y10T 29/4998* (2015.01)

(56) References Cited

U.S. PATENT DOCUMENTS

| | | | | | |
|---|---|---|---|---|---|
| 5,678,736 | A | * | 10/1997 | Hansen | 222/209 |
| 6,065,270 | A | * | 5/2000 | Reinhard et al. | 53/426 |
| 6,134,866 | A | * | 10/2000 | Schoenewolff et al. | 53/561 |
| 7,309,463 | B2 | * | 12/2007 | Hansen | 264/515 |
| 2003/0060749 | A1 | * | 3/2003 | Aneas | 604/20 |
| 2009/0124966 | A1 | * | 5/2009 | Oyama | 604/68 |

OTHER PUBLICATIONS

First Office Action from Chinese Patent Office, in corresponding application, dated Nov. 13, 2013 (with partial English translation).
Second Office Action from Chinese Patent Office, in corresponding application, dated Jul. 22, 2014 (with partial English translation).
Third Office Action from Chinese Patent Office, in corresponding application, dated Apr. 23, 2015 (with partial English translation).

* cited by examiner

PROCESS FOR PRODUCING AND ASSEMBLING A MEDICAL OPERATIONS SYRINGE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISK OR AS A TEXT FILES VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

1) Field of the Invention

The present invention concerns a process for producing and completely assembling a medical operations syringe, such as a syringe intended to contain a medical liquid to be injected or an organic liquid taken from organisms.

2) Description of Related Art

Notoriously, the syringes traditionally used to perform medical operations, such as injections or samples, include a usually cylindrical hollow body, made of plastic material, and a thrust piston, partly contained into the hollow body within which is made sliding by actuating means, (i.e., operator's hand), in order to perform medical interventions.

The thrust piston is provided at a first end with a handle head, accessible to the operator, and at a second end with a seal plunger, usually made of rubber, placed inside the hollow body and suited to come into contact with the liquid to be injected or taken during the medical operations.

In turn, the hollow body presents a main inlet at a first end, through which the thrust piston is inserted into the hollow body itself, and at a second end of a narrowing beak or neck, a hollow needle is engaged through which the injected liquid passes.

Currently, syringes for medical operations are mainly produced through a process of injection moulding, whereby the nominal essential components mentioned above, namely hollow body, thrust piston, seal plunger and needle, are obtained separately in operative steps and subsequently assembled by the operator.

This implies two main sets of drawbacks, without any doubt of not slight importance for the known technique of the field.

Firstly, in fact, the syringe assembly operations occur inevitably with some manipulation of the aforesaid components, with the obvious and consequent risk of contamination, due to exposure or contact with external agents, although operations themselves are done with extreme care and caution in an environment with a high degree of microbiological cleanliness.

This problematic issue appears in all its evidence and critical state when analyzing single-dose syringes pre-filled with medical liquid: in this case, the hollow body, thrust piston, seal plunger and needle with its needle-carrier are transferred and delivered to the producer of the drug who, after having filled the hollow body with the liquid, provides to assemble together the pieces just mentioned in a controlled atmosphere environment (so-called "white room") in order to avoid contaminating the liquid.

Although strict procedural protocols are provided, such an approach does not completely reduce the risk of contamination of both of the components and the medical liquid: not by chance, however, it is usually required the application of an additional plastic envelope to package the syringe just assembled in order to assure the highest possible aseptic conditions and, therefore, of safety in the subsequent use thereof.

Secondly, the production technology and resulting assembling system of a syringe currently used require fairly long implementation times, which, combined also with the sophisticated equipments used to ensure the maximum aseptic conditions and, therefore, safe conditions of use, determine a certain economically expensive situation which reflects in market prices less competitive than expected.

BRIEF SUMMARY OF THE INVENTION

The present invention seeks to overcome the drawbacks of the known art just complained.

In particular, primary purpose of the invention is to develop a process for producing and assembling a syringe for medical operations which ensures aseptic conditions better than those ones resulting from equivalent methods of known type, to the syringe.

In other words, main purpose of the current invention is to provide a process for producing and assembling a syringe for medical operations which, compared to the known technique, reduces the risks and level of contamination of the components of the syringe and any medical liquid contained in it.

It is a second purpose of the present invention to devise a process for producing and assembling a syringe for medical operations which, while ensuring the attainment of the abovementioned purpose, is more rapid to implement than the known processes.

Within such a second purpose, task of the invention is to give substance to a process of producing and assembling a syringe for medical operations which, the other factors at stake being equal, allows to reduce the production cost of the syringe itself compared to the state of the prior art. Said purposes are achieved through a process for producing and assembling a syringe for medical operations as to claim 1 attached, to which they refer for the sake of brevity.

Further applicative characteristics of detail of the process of the invention are highlighted by the relative dependent claims.

Advantageously, the process of the invention allows to fully arrange a syringe for medical operations, even in its minimal constructive composition, without any manipulation of the component organs of the syringe by the operator.

This allows to make a totally sterilized a syringe for medical operations and to ensure, therefore, a subsequent use thereof in optimal conditions of safety under the point of view of hygiene and health of the people involved, patients and operators.

Still advantageously, the process of producing and assembling of the invention allows to get a syringe for medical operations with a high degree of sterilization faster than processes of the known art.

Equally advantageous, this reflects in a significant reduction of the production cost of a syringe for medical operations compared to the current state of the art, of course the other factors involved being equal. In advantageous manner, moreover, the syringe for medical operations obtained with the process of producing and assembling of the invention presents features of functionality at least equivalent to those ones of known syringes compared to which it keeps, however, the benefits just outlined.

BRIEF DESCRIPTION OF THE SEVERAL VIEWS OF THE DRAWINGS

Said purposes and advantages, as well as others that will emerge later, will appear to a greater extent by the following description relating to a preferred application of the process of the invention, given as an exemplifying and illustrative, but not limitative, title with reference to the attached drawings where.

DETAILED DESCRIPTION OF THE INVENTION

Figure 10:
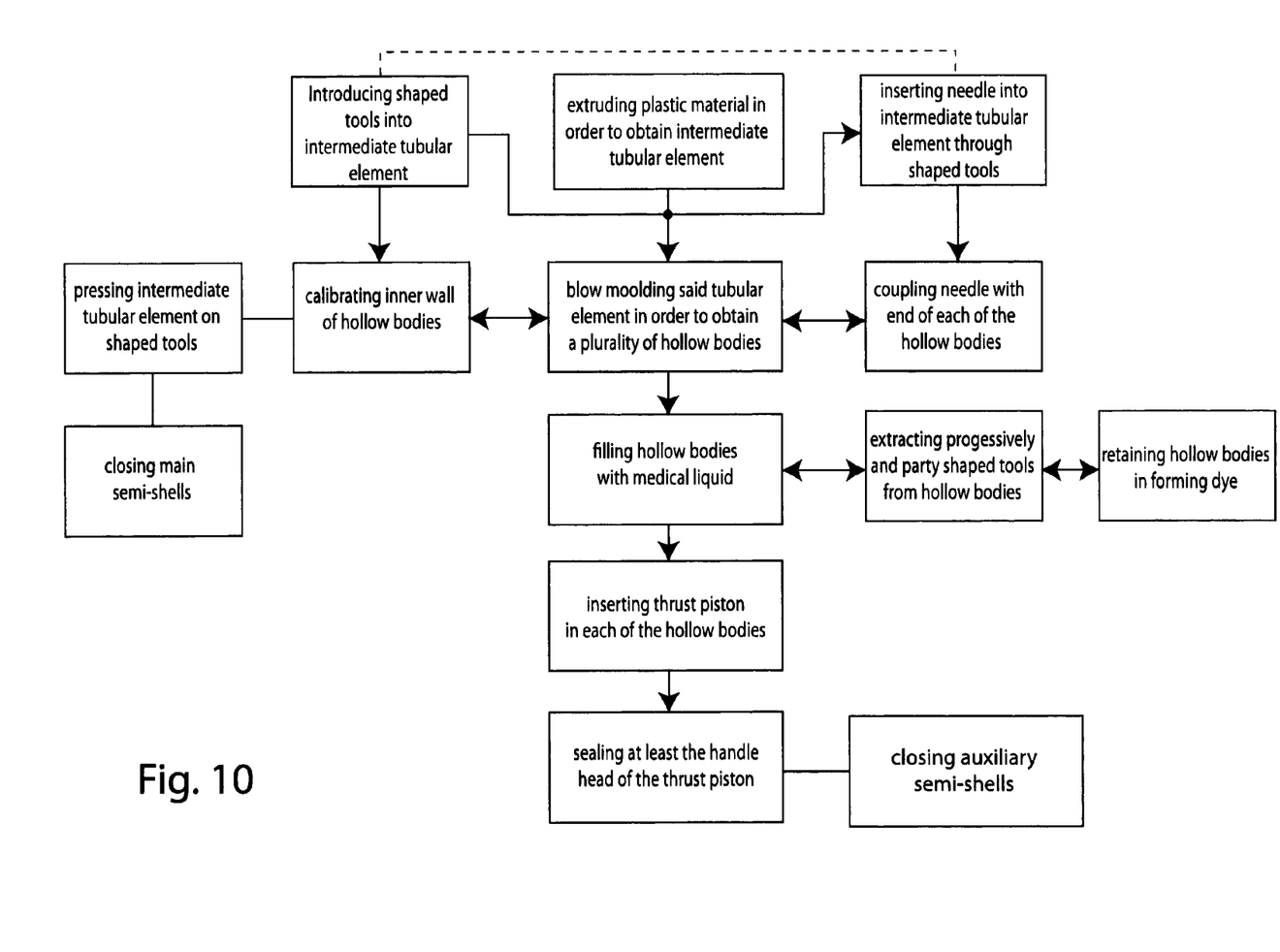
FIG. 10 is a block diagram of the process of FIGS. 1-9.

The process for producing and assembling a syringe for medical operations, injections in the specific case, object of the invention, is shown schematically in FIGS. 1-9, as well as in the block diagram of the subsequent FIG. 10.

Figure 1:
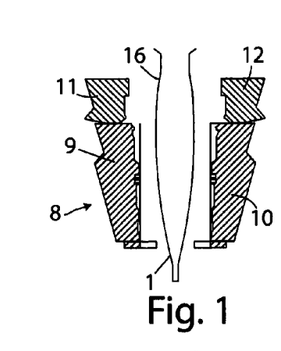
FIGS. 1-9 are schematic and simplified views of the sequential operations of the process of the invention.
Figure 4:
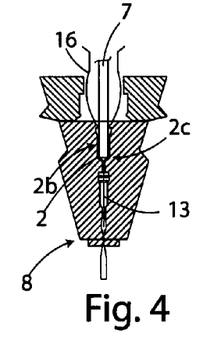
Figure 7:
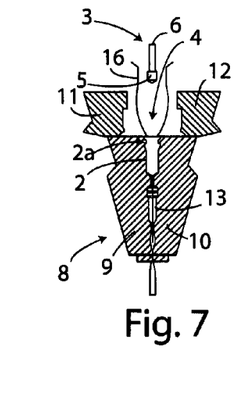
Figure 8:
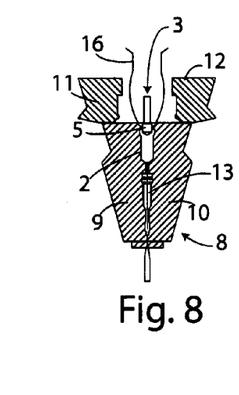
Figure 9:
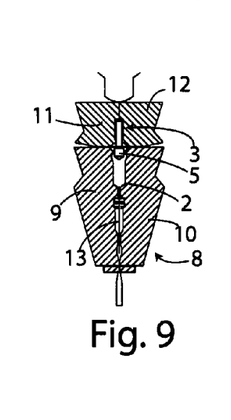

In accordance with the invention, such a process includes in the order the following operations:
- extruding plastic material at high temperature, for example 200° C., in order to obtain an intermediate tubular element 1 made of plastic material at least partially at molten state, known in jargon as "parison", according to what FIG. 1 illustrates;
- performing on the intermediate tubular element 1a blow moulding in order to obtain a plurality of hollow bodies 2, according to what indicated in FIG. 4;
- inserting firmly and at least partially a thrust piston 3 within each of the hollow bodies 2 at a time immediately following the operation of blow moulding (operation shown in FIGS. 7 and 8).

The operations of extrusion, blow moulding and insertion of the thrust piston 3 just cited take place continuously within the same industrial machinery in which ideal conditions of sterilization are kept.

In particular, the thrust piston 3 is inserted into the corresponding hollow body 2 through the main inlet 4 present at a first end 2a of the hollow body 2, positioning inside the latter at least the plunger 5 of the thrust piston 3 and leaving protruding at least the handle head 6 of the thrust piston 3 itself.

Preferably but not necessarily, the process of the invention comprises the operation of calibrating the inner wall 2b of the hollow bodies 2, performed before the operation of inserting the thrust piston 3 into its hollow body 2 and, in practice, simultaneously to the extrusion operation, while the various hollow bodies 2 are still heated and at least partially at molten and/or malleable state.

It is clear that, in other applications of the process of invention, not represented, the operation of calibrating could affect only a longitudinal stretch of the inner wall of the hollow bodies.

More specifically, the operation of calibrating the inner wall 2b of the hollow bodies 2 consists in the operation of pressing the intermediate tubular element 1 onto a series of shaped tools 7 previously introduced within the intermediate tubular element 1 just obtained through the mentioned operation of extrusion of plastic material.

Accordingly, therefore, the operation of calibrating the inner wall 2b of the hollow bodies 2 is contextual with the operation of their blow moulding, distinguishing from the latter only for the initial phase of introduction of the shaped tools 7 into the intermediate tubular element 1.

Preferably, each of the shaped tools 7 includes a cylindrical element having a mostly longitudinal development, so that the inner wall 2b of the hollow bodies 2 presents a substantially linear profile.

FIGS. 1-9 highlight that the operation of extrusion and the operation of blow moulding occur inside a forming dye 8 of the type in itself known in the field under consideration.

The forming dye 8 presents in this case a plurality of cavities, not shown for ease of reference, each of which having the outer profile which approximates the predefined shape for the respective hollow body 2.

More in detail, the forming dye 8 includes first of all two main half-shells 9, facing and opposed each other and two auxiliary half-shells 11, 12, operatively connected with the main half-shells 9, 10 in a position above them.

The forming dye 8 is open both during the operation of extrusion, keeping the main half-shells 9, 10 spaced apart from the intermediate tubular element 1, and during the operation of introducing the shaped tool 7 into the intermediate element 1, drawing up one to another the main half-shells 9, 10 and placing them close to the intermediate element 1.

Therefore, the operation of pressing the intermediate tubular element 1 onto the shaped tools 7 consists in the operation of closing the lower part of the forming dye 8 which places the main half-shells 9, 10, one close to the other interposing the intermediate tubular element 1 and shaped tools 7 for at least a longitudinal section of the half-shells 9, 10 themselves.

In a preferred but not binding way, the process of the invention includes the operation of coupling with the second end 2c, opposite to the first end 2a of each of the hollow bodies 2, an injections and sample needle 13 communicating with the internal volume 14 of the respective hollow body 2, performed simultaneously with the operation of blow moulding and operation of calibrating the inner wall 2b of the hollow bodies 2.

More precisely, the needle 13 is coupled with a narrowing beak, for the time being not shown, made in the second end 2c of each of the hollow bodies 2 through the forming dye 8.

Figure 2:
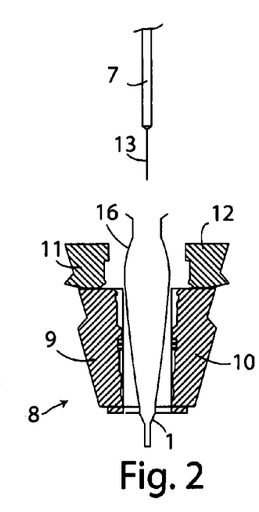
Figure 3:
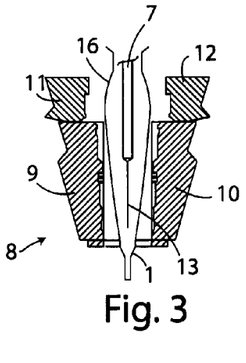

In this respect, the process of the invention includes the preparatory operation, visible in FIGS. 2 and 3, of inserting, by means of the shaped tools 7, the needle 13 into the intermediate tubular element 1, performed before the proper operation of coupling the needle 13 with the second end 2c of the corresponding hollow body 2 and simultaneously with the operation of introducing the shaped tools 7 within the intermediate tubular element 1.

Figure 6:
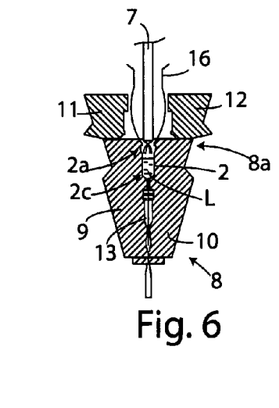

According to the preferred application here described of the invention, the process includes the operation, illustrated in FIG. 6, of filling the hollow bodies 2 with a medical liquid L in order to obtain pre-filled and single-dose syringes, one of which clearly visible apart in FIGS. 11-14 where it is overall numbered with 20.

The operation of filling the hollow bodies 2 with the medical liquid L is performed after the operation of blow moulding the hollow bodies 2 and before the operation of inserting the thrust piston 3 into a respective hollow body 2.

The process also includes the operation of extracting progressively and partially the shaped tools 7 from the hollow bodies 2 for a prefixed length, performed during the operation of filling the hollow bodies 2 themselves, suitable to define the volume available for the medical liquid L inside the hollow bodies 2.

Figure 5:
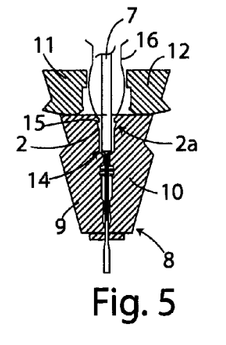

Before extracting or drawing back the shaped tools 7 from the hollow bodies 2, the process of the invention provides a partial opening of the forming dye 8, as shown in FIG. 5, in order to facilitate and make effective such an extraction operation: the opening of the forming dye 8 consists in removing one from the other the main half-shells 9, 10 of a predetermined distance, in the order of a few tenths of a millimeter.

Other applications of the process of invention, not illustrated in the attached drawings, may provide that the operation of extracting the shaped tool from the hollow body occurs by keeping the forming dye closed.

Advantageously, the process of the invention comprises the operation of retaining within the forming dye 8 the hollow bodies 2 that have just been formed. This operation is performed after the operation of blow moulding and during the operation of extracting the shaped tools 7 from the hollow bodies 2.

This operative trick prevents the shaped tools 7, during the backing movement from the hollow bodies 2 to, drag disadvantageously with them the hollow bodies 2 themselves, thus avoiding compromising the structural integrity of the latter.

Such an operation of retaining the hollow bodies 2 takes place preferably through an annular bar undercut 15 made in the inner surface of the end 8a of the forming dye 8.

It is understood that, in additional applications of the process of the invention, not represented here, the operation of retaining the hollow bodies may occur through only one bar undercut or through several undercuts separate and distinct each other.

Moreover, in other application solutions of the process of the invention, yet not illustrated in the drawings that follow, the operation of retaining the hollow bodies just formed by blow moulding can occur resorting to other operating tricks or alternative systems and apparatus.

In advantageous manner, the process of the invention includes, at purely preferential title, the operation of sealing the handle head 6 and a central portion, protruding from the respective hollow body 2, of the thrust piston 3, performed after the operation of inserting firmly and at least partially the thrust piston 3 into the hollow body 2.

This operation of sealing determines, in essence, the packaging of the syringe for medical operations 20 without interruption with respect to the other operations described above involving the production and complete assembly of the syringe 20 itself.

In this way, the invention obtains a further advantage over the equivalent known technique, in case of single-dose pre-filled syringes for injections. Indeed, the execution of the operation of sealing the portion of the thrust piston 3 protruding from the relative hollow body 2 directly in manufacturer's plant of the syringe 20 virtually eliminates the final packaging operation carried out today on the known syringes from the producer of the medical liquid.

Consequently, this aspect of the invention helps to reduce, compared to the current state of the art handling of the syringe or its component organs by the operators, limiting the risks of contamination very much in both of the same organs and the medical liquid introduced into the hollow body of the syringe, as well as to make the work of completely setting up of the syringe easier and quicker.

The operation of sealing the handle head 6 and portion of the thrust piston 3 which protrudes from each of the hollow bodies 2 consists in the operation of closing the upper part, nominally the auxiliary half-shells 11, 12, of the forming dye 8: through such an operation, a section of the free portion 16 of the intermediate tubular element (parison) 1 made of plastic material is pressed against the outer surface of the handle head 6 and the protruding portion of the thrust piston 3.

In addition, it is stated precisely that the entire process just described, consisting of the operations of extruding the intermediate element 1, blow moulding in order to obtain the hollow bodies 2, calibrating the inner wall 2b of each of these, coupling a needle 13 with each of the hollow bodies 2, filling the hollow bodies 2, inserting a thrust piston 3 into each hollow body 2 and sealing at least its handle head 6, occur in a total time not exceeding 20 seconds.

Finally, it is stressed that the operations of blow moulding, calibrating the inner wall 2b of the hollow bodies 2, coupling the needle 13 with each of the hollow bodies 2 and filling the hollow bodies 2 are performed through the shaped tools 7.

In fact, each shaped tool 7 is provided with a nozzle, not shown, which, besides being used to calibrate the inner wall 2b of the hollow body 2 with which it comes into contact, is also used to blow air and carried out, in practice, the blow moulding of such a hollow body 2 and subsequently filling it with the medical liquid L.

Furthermore, as mentioned above, each shaped tool 7 is used to support the needle 13 while it is introduced into the intermediate tubular element 1. Beyond to calibrate the inner wall 2b of the hollow 2, the shaped tools 7 allow thus to get another advantage of not negligible relevance compared to the current state of the art.

Indeed, in calibrating the inner wall 2a, the shaped tools 7 cool down the plastic material and, most importantly, the same inner wall 2b of the hollow bodies 2 which are forming.

In this way, the process of the invention produces more rapidly than the known art the ideal conditions of absence or at least maximum reduction of the risks of biological contamination for the medical liquid L which is housed in the various hollow bodies 2.

If it is considered that the hollow bodies of syringes are often filled with thermolabile chemical or biological products, so sensitive to heat up to the point of losing their own qualities, the advantage brought by the present invention is immediately apparent.

For these products, therefore, the invention reduces the waiting time for the introduction of the liquid product into the medical container, with the obvious advantages that this implies in terms of productive efficiency. Alternative applications of the process of the invention, not shown, may provide that only one or some of the operations of blow moulding, calibrating the inner wall of the hollow bodies, coupling a needle with each of the hollow bodies and filling the hollow bodies are performed through the shaped tool.

Subsequent FIGS. 11-14 represent the syringe for medical operations 20, notably for injections, directly produced by the process just described and, as such, itself subject of protection by the present invention.

As it can be noted, the syringe for injections 20 develops along a longitudinal axis of symmetry Y and includes the hollow body 2, the thrust piston 3 equipped with the plunger 5 and handle head 6 projecting from the hollow body 2.

The syringe 20 also includes the needle 13, coupled at the end 13a with the narrowing beak 17 of the hollow body 2 through junction means, consisting of the plastic material which, still at molten state, is pressed between the main half-shells 9, 10 of the forming dye 8 during the process of blow moulding.

The needle 13 is also completely covered with protection means, overall numbered with 18, applied externally to the needle 13 and made monolithic with the hollow body 2 during the aforesaid process of blow moulding, which produce in practice a sort of cap for the needle 13 in non-use conditions of the syringe 20.

More in particular, the protection means 18 comprise a laminar capsule made of plastic material which, at the hollow body 2, includes break means, not visible, so as to allow its practical, easy and quick detachment from the hollow body 2 when the syringe 20 must be used.

FIGS. 11-14 highlights, moreover, that, according to the preferred embodiment described herein of the invention, the syringe for injections 20 also comprises sealing means, as a whole indicated with 19, also made monolithic with the hollow body 2 due to the closure of the auxiliary half-shells 11, 12 of the forming dye 8 during the final part of the process of production and assembly of the invention.

The sealing means 19 cover or close the portion of the thrust piston 3 which, in non-use conditions of the syringe 20, protrudes from the hollow body 2.

Figures 11, 12, 13, 14:
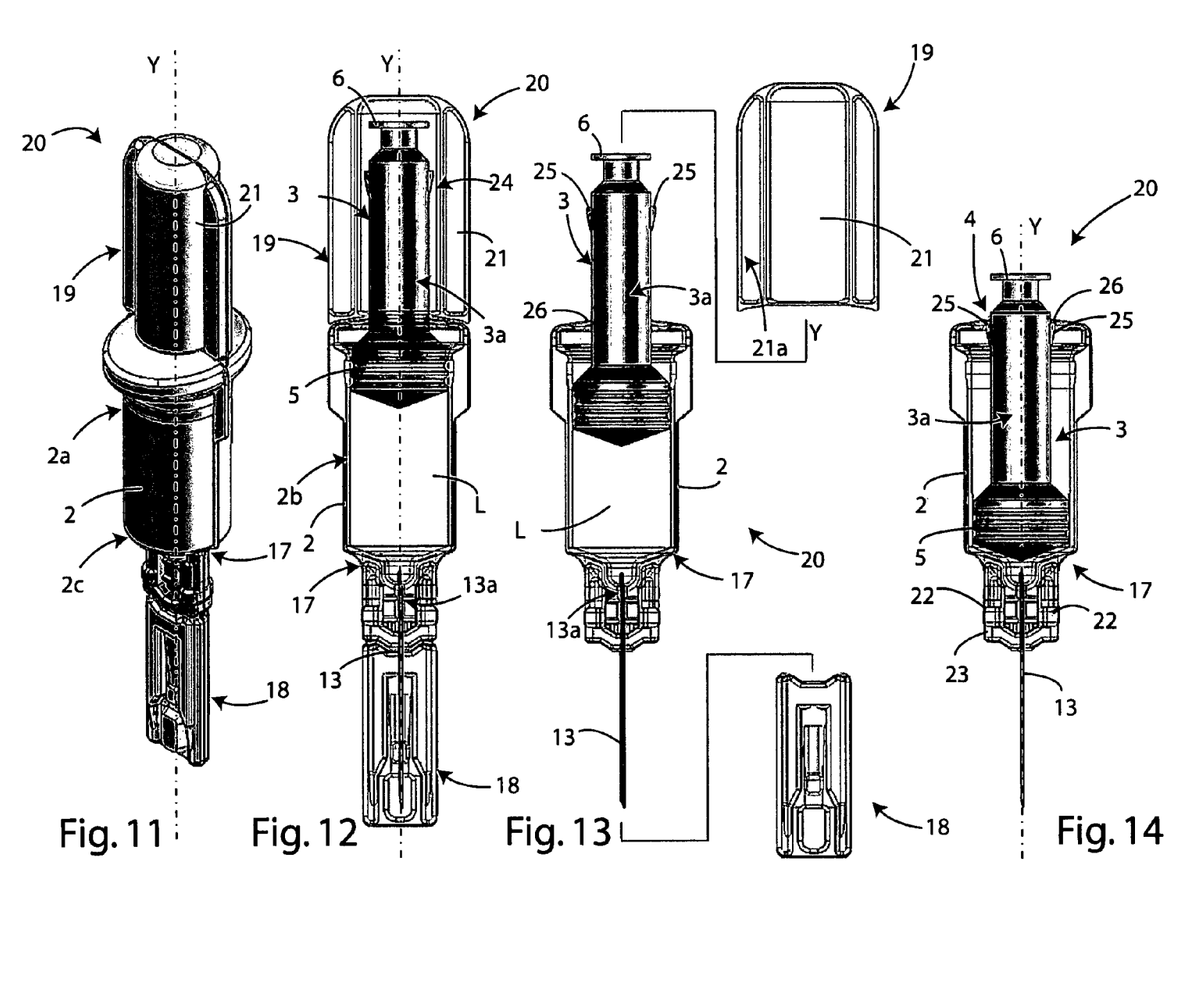
FIG. 11 is the assonometric view of the syringe for medical injections obtained by the process of FIGS. 1-9.
FIG. 12 is the longitudinal section of FIG. 11.
FIG. 13 is the exploded view of FIG. 12.
FIG. 14 is the syringe of FIG. 13 immediately after use.

As a matter of fact, therefore, the syringe 20 obtained by the process of invention is already packaged, according to the configuration shown in FIGS. 11 and 12, and does not require additional operations, processes or treatments to be placed on the market, if not filling with the medical liquid in case it is produced and marketed empty.

The sealing means 19 includes a laminar lid 21 which, as FIG. 13 shows, the operator separates easily, turning it around the longitudinal axis Y, from the hollow body 2 when he intends to arrange the syringe 20 in the conditions, shown in FIG. 14, of performing an injection on a patient. Conveniently, if the syringe 20 is disposable, the laminar lid 21 is used to cover the needle 13 as soon as the injection has been completed and thus serve as an additional safety cap in order to prevent accidental and sometimes very dangerous contacts of people with the needle 13 already used.

In this regard, the inner wall 21a of the laminar lid 21 includes raised projections, not shown, which are snap forced inside respective grooves 22, shown in FIG. 14 and made in the needle-carrier insert 23 fixed to the hollow body 2, in order to match the laminate lid 21 to the needle 13. Preferably but not necessarily, the syringe 20 includes retention means, as a whole indicated with 24, suitable to keep the thrust piston 3 firmly within the hollow body 2 when the medical operation is completed.

More in detail, the retention means 24 comprise an annular wing or a plurality of shaped wings 25 protruding from the outer wall 3a of the thrust piston 3, and an annular edge 26 positioned at the inlet 4, opposite to the narrowing beak 17 of the hollow body 2.

From the description just made, it is understood, therefore, that the process for producing and assembling a syringe for medical operations, object of the present invention, achieves the purposes and reaches the advantages mentioned above.

In execution phase, changes can be made to the process of the invention consisting, for example, in obtaining a single hollow body through the operation of blow moulding, for instance using a single cavity forming dye. In such a case, the operative modes of the process of the invention described above will vary accordingly.

Furthermore, the thrust piston could be inserted into the respective hollow body of a stretch longer than that one previously described, so that only the handle head remains protruding from the hollow body to be handled by the operator.

It is also stated precisely that the present invention, despite having been described with particular reference to a disposable pre-filled syringe for injections, also extends to empty syringes used both for injections and other medical operations, such as samples of blood or other liquid from the human or animal body.

It is clear that numerous other variations can be made to the process in question, without for this reason going out of the novelty principles inherent to the inventive idea here expressed, as it is clear that, in the practical implementation of the invention, materials, shapes and sizes of the illustrated details can be any, as needed, and replaced with others technically equivalent.

Where the constructive features and the techniques mentioned in the following claims are followed by reference numbers or signs, those reference signs have been introduced with the sole objective of increasing the intelligibility of the claims themselves and therefore they have no limiting effect on the interpretation of each element identified, by way of example only, by these reference signs.

The invention claimed is:

1. A process for producing and assembling a medical operations syringe comprising in the order of at least the following operations:
   extruding plastic material in order to obtain an intermediate tubular element of plastic material at least partially at molten state;
   performing on said intermediate tubular element a blow moulding in a forming mould in order to obtain at least a hollow body having an inner wall wherein said blow moulding is carried out by pressing the intermediate tubular element on at least one shaped tool and carrying out the operation of blow moulding through said at least one shaped tool;
   calibrating at least a longitudinal stretch of the inner wall of said hollow body performed contextually with said operation of blow moulding, while said hollow body is still heated and at said at least partially molten or malleable state so that said inner wall presents a substantially linear profile;
   inserting firmly and at least partially a thrust piston into said hollow body immediately after said blow moulding operation, wherein said operation of calibrating said inner wall of said hollow body consists of the operation of pressing said intermediate tubular element on the at least one shaped tool previously introduced within said intermediate tubular element obtained through said operation of extruding plastic material;

wherein said operations of extrusion, blow moulding and insertion of said thrust piston takes place continuously within one installation of industrial machinery in which conditions of sterilization are maintained.

2. The process as defined in claim 1, characterized in that said thrust piston is inserted into said hollow body through a main inlet present at a first end of said hollow body, positioning within said hollow body at least a plunger of said thrust piston leaving protruding at least a handle head of said thrust piston.

3. The process as defined in claim 1, characterized in that said operation of extrusion and said operation of blow moulding occur within said forming mould which presents one or more cavities each of which having an outer profile which approximates a predefined shape for said hollow body, said mould being composed of at least two main half-shells facing and opposed to each other.

4. The process as defined in claim 3, characterized in that said forming mould is open both during said extrusion operation, keeping said main half-shells spaced apart from said intermediate tubular element, and during the operation of introducing said shaped tool into said intermediate tubular element, drawing up one to another said main half-shells and placing them close to said intermediate tubular element.

5. The process as defined in claim 3, characterized in that said operation of pressing said intermediate tubular element onto said shaped tool consists in an operation of closing said forming mould which places said main half-shells one close to the other interposing said intermediate tubular element and said shaped tool for at least a longitudinal section of said main half-shells.

6. The process as defined in claim 5, characterized in that it includes the operation of sealing at least a handle head of said thrust piston, performed after the operation of inserting firmly and at least partially said thrust piston into said hollow body, suitable to accomplish the packaging of said medical operations syringe.

7. The process as defined in claim 6, characterized in that said operation of sealing at least said handle head of said thrust piston consists in an operation of closing two auxiliary half-shells belonging to said forming mould, whereby at least one section of a free portion of said intermediate tubular element made of plastic material is pressed against an outer surface of at least said handle head of said thrust piston.

8. The process as defined in claim 6, characterized in that said operations of extruding, blow moulding, calibrating said inner wall, and an operation of coupling said needle, filling said hollow body, inserting said thrust piston and sealing at least said handle head occur in a total time not exceeding 20 seconds.

9. The process as defined in claim 3, characterized in that it includes an operation of coupling with a second end of said hollow body, opposite to a first end, an injections and or samples needle communicating with an internal volume of said hollow body, performed simultaneously with said operation of blow moulding and said operation of calibrating said inner wall of said hollow body.

10. The process as defined in claim 9, characterized in that it includes an operation of inserting said needle into said intermediate tubular element by means of said shaped tool, performed before the operation of coupling said needle with said second end of said hollow body and simultaneously with said operation of introducing said shaped tool into said intermediate tubular element.

11. The process as defined in claim 3, characterized in that it comprises an operation of filling said hollow body with a medical liquid, performed after the operation of blow moulding said hollow body and before the operation of inserting said thrust piston into said hollow body.

12. The process as defined in claim 11, characterized in that it includes an operation of extracting, progressively and partially, said shaped tool from said hollow body for a prefixed length, performed during said operation of filling said hollow body, suitable to define the volume available for said medical liquid introduced into said hollow body.

13. The process as defined in claim 12, characterized in that it comprises an operation of retaining said hollow body within said forming mould just formed, performed after said operation of blow moulding and during said operation of extracting said shaped tool from said hollow body.

14. The process as defined in claim 3, characterized in that at least operations of coupling said needle with said hollow body and filling said hollow body are performed through said shaped tool.

15. A process for producing and assembling a medical operations syringe comprising in the order of at least the following operations:
    extruding plastic material in order to obtain an intermediate tubular element of plastic material at least partially at molten state;
    performing on said intermediate tubular element a blow moulding in a forming mould in order to obtain at least a hollow body having an inner wall wherein said blow moulding is carried out by pressing the intermediate tubular element on at least one shaped tool and carrying out the operation of blow moulding through said at least one shaped tool;
    calibrating at least a longitudinal stretch of the inner wall of said hollow body performed contextually with said operation of blow moulding, while said hollow body is still heated and at said at least partially molten or malleable state so that said inner wall presents a substantially linear profile;
    coupling a tool and an injection or sample needle communicating with an internal volume of said hollow body, with a second end of said hollow body, opposite to a first end, simultaneously with said operation of blow moulding and said operation of calibrating said inner wall of said hollow body;
    inserting firmly and at least partially a thrust piston into said hollow body immediately after said blow moulding operation, and applying protection means to said tool and injection or sample needle wherein said operation of calibrating said inner wall of said hollow body consists of the operation of pressing said intermediate tubular element on the at least one shaped tool previously introduced within said intermediate tubular element obtained through said operation of extruding plastic material; wherein said operations of extrusion, blow moulding, insertion of said thrust piston and applying protection means to said tool and/or injection or sample needle takes place continuously within one installation of industrial machinery in which conditions of sterilization are maintained.

16. A process for producing and assembling a medical operations syringe comprising in the order of at least the following operations:
    extruding plastic material in order to obtain an intermediate tubular element of plastic material at least partially at molten state;
    performing on said intermediate tubular element a blow moulding in a forming mould in order to obtain at least a hollow body having an inner wall; wherein said blow moulding is carried out by pressing the intermediate tubular element on at least one shaped tool and carrying out the operation of blow moulding through said at least one shaped tool;

calibrating at least a longitudinal stretch of the inner wall of said hollow body performed contextually with said operation of blow moulding, while said hollow body is still heated and at said at least partially molten or malleable;

inserting firmly and at least partially a thrust piston into said hollow body immediately after said blow moulding operation, wherein said operation of calibrating said inner wall of said hollow body consists of the operation of pressing said intermediate tubular element on the at least one shaped tool previously introduced within said intermediate tubular element obtained through said operation of extruding plastic material; wherein said operations of extrusion, blow moulding and insertion of said thrust piston takes place continuously within one installation of industrial machinery in which conditions of sterilization are maintained wherein said operation of extrusion and said operation of blow moulding occur within said forming mould which presents one or more cavities each of which having an outer profile which approximates a predefined shape for said hollow body, said mould being composed of at least two main half-shells facing and opposed to each other; and wherein said operation of pressing said intermediate tubular element onto said shaped tool consists in the operation of closing said forming mould which places said main half-shells one close to the other interposing said intermediate tubular element and said shaped tool for at least a longitudinal section of said main half-shells and including an operation of sealing at least a handle head of said thrust piston, performed after the operation of inserting firmly and at least partially said thrust piston into said hollow body, suitable to accomplish packaging of said medical operations syringe and operations of extruding, blow moulding, calibrating said inner wall, and an operation of coupling said needle, filling said hollow body, inserting said thrust piston and sealing at least said handle head occur in a total time not exceeding 20 seconds.

* * * * *